(12) United States Patent
Patel et al.

(10) Patent No.: US 7,087,089 B2
(45) Date of Patent: Aug. 8, 2006

(54) GRAFT PROSTHESIS DEVICES CONTAINING RENAL CAPSULE COLLAGEN

(75) Inventors: Umesh H. Patel, West Lafayette, IN (US); Michael C. Hiles, Lafayette, IN (US); Jason P. Hodde, West Lafayette, IN (US)

(73) Assignee: Cook Biotech Incorporated, West Lafayette, IN (US)

( * ) Notice: Subject to any disclaimer, the term of this patent is extended or adjusted under 35 U.S.C. 154(b) by 0 days.

(21) Appl. No.: 10/186,150

(22) Filed: Jun. 28, 2002

(65) Prior Publication Data

US 2003/0014126 A1 Jan. 16, 2003

Related U.S. Application Data

(60) Provisional application No. 60/301,671, filed on Jun. 28, 2001.

(51) Int. Cl.
*A61F 2/02* (2006.01)
(52) U.S. Cl. .................. 623/23.72; 623/1.47; 523/105; 424/572
(58) Field of Classification Search ............... 623/1.47, 623/23.72, 23.47; 523/105, 103; 530/356; 424/572
See application file for complete search history.

(56) References Cited

U.S. PATENT DOCUMENTS

| 2,127,903 | A | | 8/1938 | Bowen | |
|---|---|---|---|---|---|
| 4,502,159 | A | * | 3/1985 | Woodroof et al. | ......... 623/1.41 |
| 4,801,299 | A | * | 1/1989 | Brendel et al. | ............ 623/1.47 |
| 4,829,000 | A | | 5/1989 | Kleinman et al. | |
| 4,902,508 | A | | 2/1990 | Badylak et al. | |
| 4,956,178 | A | | 9/1990 | Badylak et al. | |
| 5,127,903 | A | | 7/1992 | Mailot et al. | |
| 5,275,826 | A | * | 1/1994 | Badylak et al. | ............. 424/551 |
| 5,281,422 | A | | 1/1994 | Badylak et al. | |
| 5,352,463 | A | | 10/1994 | Badylak et al. | |
| 5,645,860 | A | | 7/1997 | Knapp, Jr. et al. | |
| 5,674,290 | A | * | 10/1997 | Li | ................................. 623/1 |
| 5,756,350 | A | * | 5/1998 | Lee et al. | ................... 435/325 |
| 5,936,256 | A | * | 8/1999 | Fedorov et al. | ......... 252/182.13 |
| 6,696,074 | B1 | * | 2/2004 | Dai et al. | .................... 424/423 |
| 2002/0146393 | A1 | * | 10/2002 | Bell et al. | .................. 424/93.1 |
| 2005/0027348 | A1 | * | 2/2005 | Case et al. | ................. 623/1.24 |

FOREIGN PATENT DOCUMENTS

| WO | WO96/24661 | 8/1996 |
|---|---|---|
| WO | WO 96/25179 | 8/1996 |
| WO | WO 98/22158 | 5/1998 |
| WO | WO 98/25636 | 6/1998 |
| WO | WO 98/25637 | 6/1998 |

OTHER PUBLICATIONS

RU 2186572 abstract, Yu et al, Aug. 10, 2002.*

* cited by examiner

*Primary Examiner*—Corrine McDermott
*Assistant Examiner*—Thomas J. Sweet
(74) *Attorney, Agent, or Firm*—Woodard, Emhardt, Moriarty, McNett and Henry LLP

(57) ABSTRACT

The invention provides tissue graft compositions comprising collagen-based extracellular matrices derived from renal capsules of warm-blooded vertebrates. The invention further provides a process of harvesting and purifying a renal capsule to provide an extracellular matrix material having beneficial use as a tissue graft and/or cell growth material.

26 Claims, 1 Drawing Sheet

GRAFT PROSTHESIS DEVICES CONTAINING RENAL CAPSULE COLLAGEN

REFERENCE TO RELATED APPLICATION

This application claims the benefit of U.S. Provisional Patent Application, Ser. No. 60/301,671 entitled GRAFT PROSTHESIS DEVICES CONTAINING RENAL CAPSULE COLLAGEN filed Jun. 28, 2001, which is hereby incorporated by reference herein in its entirety.

FIELD OF THE INVENTION

The present invention relates generally to graft prosthesis devices, and more particularly to such devices comprising collagen derived from extracellular matrices.

BACKGROUND OF THE INVENTION

Tissue graft materials have attained considerable clinical and economic significance today. It is now well known that collagen-based extracellular matrices (ECMs) derived from warm-blooded vertebrates can be used advantageously as tissue grafts materials. See U.S. Pat. Nos. 4,902,508 and 5,281,422, and International Publication Nos. WO 98/25636 and WO 98/22158. It has been found that collagen-based ECMs can serve as a scaffold on which animal tissues may grow. It has been also found that the materials enhance wound healing, promote endogenous tissue growth, stimulate cell proliferation and induce cell differentiation. Additionally, implants which are made from collagen-based ECMs are absorbed by the body in time and do not have to be removed once applied. The collagen-based ECMs described in the above patents and publications are also characterized by excellent mechanical properties, and effective porosity index which allow them to be used beneficially for vascular graft and connective tissue graft constructs. Furthermore, collagen-based ECMs can be fluidized by comminuting and/or enzymatic digestion, without loss of their apparent positive cell growth promoting properties.

At present, collagen-based ECM materials have been formed into and used as implants and grafts to replace or repair damaged or diseased blood vessels, ligaments, tendons, skin and urinary tract, to name a few examples. Additionally, fluidized ECMs have been proposed for injectable tissue grafts and also for topical applications. See, U.S. Pat. No. 5,275,826 and International Publication No. WO 98/22158. Furthermore, it has been suggested that collagen-based ECMs can be utilized as a cell growth substrate for growing eukaryotic cells in vitro.

Collagen-based ECMs have been harvested from various tissues of warm-blooded vertebrates. To date, various sources for collagen-based ECMs have been identified, including the submucosa of the intestinal, alimentary, respiratory, urinary, genital tracts, and stomachs and the basal membrane of livers of vertebrates. Among the above-mentioned sources, the collagen extracellular component is either an internal layer or a tightly bounded layer of the tissue/organ so that the collagen-based ECM has to be isolated. See U.S. Pat. No. 4,956,178, and International Publication Nos. WO 98/25637 and WO 98/25636. The isolation step generally involves either a de-lamination or a cell dissociation, which complicates the preparatory process and also risks disruption of the native structure of the extracellular component.

In view of the background in this area, there exists a need for collagen-based extracellular matrix materials that are readily isolated and exhibit beneficial properties for applications in tissue grafting, cell growth, and potentially other areas. The present invention addresses these needs.

SUMMARY OF THE INVENTION

One feature of the present invention relates to the discovery and provision of new tissue graft prosthesis devices formed using extracellular matrices derived from collagenous organ capsule tissue. Preferred tissue graft devices of the invention include collagen derived from renal capsules of warm-blooded vertebrate animals. The capsular tissue utilized in the invention can be isolated, rendered substantially free of cells of the animal from which it is isolated, and processed to yield extracellular matrix materials having beneficial medical and other uses.

In another aspect, the invention concerns a preparative procedure for forming a tissue graft material, the procedure including the steps of providing isolated renal capsular tissue, and decellularizing the tissue to provide the tissue graft material. Preferred processes involve contacting the tissue with a decellularizing agent, for example a cell-lysing solution. The decellularizing agent and any other processing agents can then subsequently be removed, for example by contact with rinsing and/or extraction solvents. Preparative processes will desirably result in a purified capsular material that is effective for supporting cellular growth.

One object of the present invention is to provide new tissue graft compositions and prosthesis devices, and methods for their preparation.

Another object of the invention is to provide new methods for tissue grafting.

Another object of the invention is to provide new extracellular matrix materials useful for supporting cell growth in vivo and in vitro.

Related objects and advantages of the present invention will be apparent from the following description.

DESCRIPTION OF THE PREFERRED EMBODIMENTS

Figure 1:
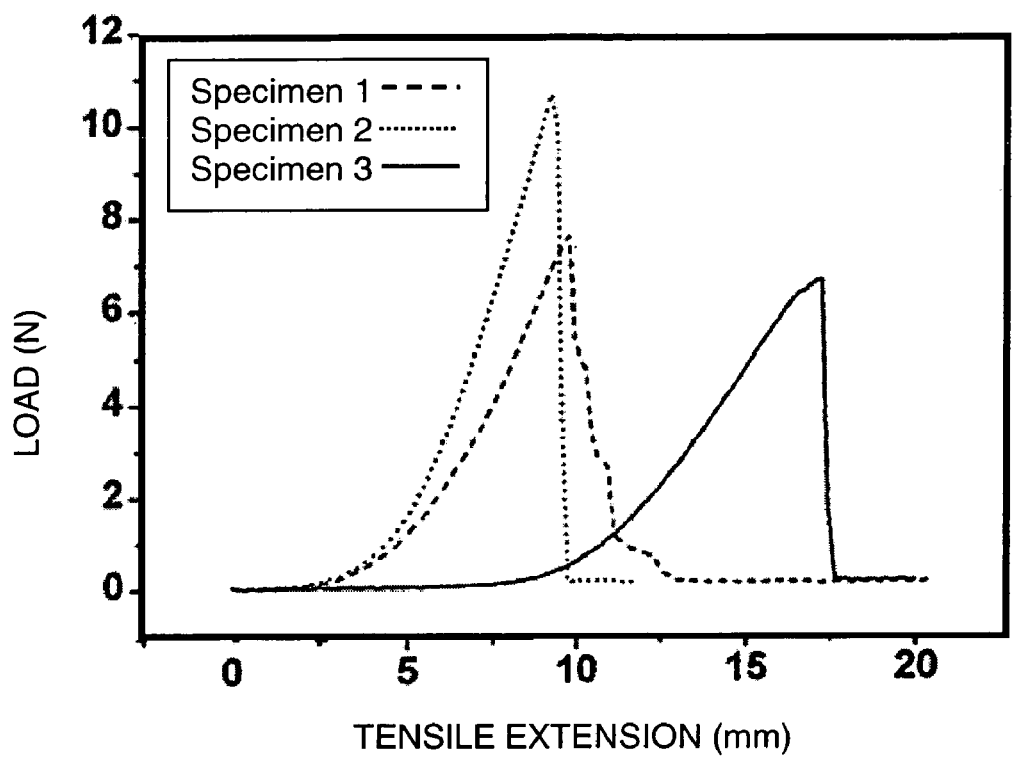
FIG. 1 provides a plot of the load required to maintain the pulling speed vs. the elongation of specimens as described in Example 4 below.

For the purposes of promoting an understanding of the principles of the invention, reference will now be made to certain embodiments thereof and specific language will be used to describe the same. It will nevertheless be understood that no limitation of the scope of the invention is thereby intended. Any alterations and further modifications in the described embodiment, and any further applications of the principles of the invention as illustrated herein being contemplated as would normally occur to one skilled in the art to which the invention relates are also included.

The present invention generally provides new graft prosthesis devices based upon collagen-containing extracellular matrices (ECMs) derived from capsular tissues, and in particular from renal capsules of warm-blooded vertebrates. The invention further provides methods for obtaining, and purifying the capsular ECMs and manufacturing various tissue grafts from the same.

Renal or kidney capsules are outer coverings enclosing the kidneys. The capsule consists of the following layers: mesothelium, dense connective tissue containing collagen strata and elastic networks, and one or more sheets of squamous cells separated from the connective tissue by a thick basal lamina. See R. E. Bulger, "Rat Renal Capsule: Presence of Layers of Unique Squamous Cells," Anatomical Record, 1973; 177:393–408. The capsule closely invests and is connected to the organ through numerous fine processes of loose connective tissue and small blood vessels.

The preferred renal capsules for the derivation of the collagen-based ECMs according to the present invention are harvested from warm-blooded vertebrates, such as mammals, preferably from porcine, bovine, or ovine, more preferably from adult pigs, and most preferably from mature adult pigs weighing greater than about 350 pounds. These renal capsules can be harvested from transgenic animals or non-transgenic animals, for example animals raised for meat production. Thus, there is an inexpensive commercial source of renal capsule for use in preparation of the tissue graft compositions in accordance with the present invention.

The capsular material can be easily isolated from the organ. In accordance with one embodiment of the present invention, kidneys, including the renal capsules, are obtained from newly slaughtered pigs. The fatty tissue attaching to the capsular tissue can be removed using a blunt dissection tool. The capsule, even though it envelopes the kidney, is attached to the kidney at discrete locations, and is fairly loose. Careful dissection will prevent the tearing of the capsule at the attachment sites. In one harvest mode, a single slit can be made in the capsule along the long axis of the kidney around the renal pelvis and the capsule can be peeled away from the renal tissue and the attaching mesenteric tissues. This longitudinal cut yields a more evenly dimensioned renal capsule film and is hence preferred. However, other dissection directions may be chosen without deviating from the scope of the invention. The separated renal capsule tissue is semi-translucent, and appears macroscopically as a single film of collagen-based extracellular matrix. Although size of the isolated renal capsule will vary from animal to animal, and species to species, porcine renal capsules taken from adult pigs are typically obtainable as collagenous sheets of about 5–15 cm in length and about 10–25 cm in width, and more typically about 10–20 cm in width.

The capsular film can be decellularized, sterilized or otherwise processed to yield a sheet of purified renal capsule ECM, for example achieving a material that is medically acceptable or of a technical grade suitable for research purposes. It will be appreciated by those skilled in the art that many conventional cell-lysing or other cell removal techniques may be used to decellularize the isolated renal capsules. A decellularizing technique which does not affect the mechanical strength and retains advantageous cell-growth promoting properties of the renal capsule ECM is preferred.

The preferred decellularization and/or other purification processes of the invention will involve contacting the renal capsule tissue with an appropriate agent or agents. For example, and not by way of limitation, this may include tanning with glutaraldehyde and formaldehyde, salt washes, such as 1.0 N saline or EDTA or ammonium chloride, contacting with a chelating agent, acids, bases and/or ionic or non-ionic detergents, such as Triton X-100, TWEEN detergents or sodium dodecyl sulfate, treatment with enzymes, such as phospholipases or dispase treatment with oxidizing compounds, gas plasma sterilization, gamma radiation, and combinations thereof. In this regard, desirable processes of the invention involve exposing the isolated renal capsule tissue to a solution containing one or more oxidizing agents, preferably peroxy compounds, more preferably organic peroxy compounds, and most preferably peracids. When a peracid is used, it is desirably selected from the group consisting of peracetic acid, perpropionic acid and perbenzoic acid. Peracetic acid is most preferred. Other peroxy disinfecting agents, for example, hydrogen peroxide, are also suitable for use. Still other suitable peroxy compounds are described in "Peroxygen Compounds", S. Block, in *Disinfection, Sterilization and Preservation*, S. Block, Editor, 4$^{th}$ Edition, Philadelphia, Lea & Febiger, pp. 167–181, 1991; and "Disinfection with peroxygens" M. G. C. Baldry and J. A. L. Fraser, in *Industrial Biocides*, K. Payne, Editor, New York, John Wiley and Sons, pp. 91–116, 1988. While peroxy compounds are preferred, other oxidizing agents, for example, chlorine agents such as chlorhexidine (1,6-di(4-chlorophenyldiguanido)hexane) in its digluconate form may also be used. Many other suitable chlorine agents are described in "Chlorhexidine", G. W. Denton, in *Disinfection, Sterilization and Preservation*, S. Block, Editor, 4$^{th}$ Edition, Philadelphia, Lea & Febiger, pp. 274–289, 1991.

The preferred solvent for diluting the oxidizing agent is aqueous alcohol. Preferably the alcohol content is from about 1% to about 30% by volume of the solution, and more preferably the alcohol content is between about 2% to about 10% by volume. It is contemplated that many alcohols may be used to form the aqueous alcohol solution. However, it is preferred that the alcohol contains from 1 to about 6 carbon atoms; more preferred that the alcohol is selected from a group consisting of ethanol, propanol, isopropanol, denatured alcohol and butanol; and most preferred that the alcohol is either ethanol or denatured alcohol. In addition, the solution preferably has a pH of about 1.5 to about 10, more preferably a pH of about 2 to about 6, and most preferably a pH of about 2 to about 4. Although not necessary, conventional buffers may be used to adjust the pH, and the choice of buffers is within the knowledge of those skilled in the art.

The isolated renal capsule tissue will be exposed to the decellularizing or other processing agent for a suitable period of time. Generally, exposure can entail submersing the isolated renal capsule into a solution under agitation. The exposure time is typically at least about 5 minutes, for example in the range of about 15 minutes to about 40 hours, and more typically in the range of about 0.5 hours to about 8 hours. Also, preferably, the renal capsular tissue is pre-rinsed with a solvent, for example sterile water, before exposure to the processing solution.

One preferred purification procedure of the invention is exposing the renal capsular film to dilute peracetic acid. The peracetic acid is diluted with an aqueous alcohol solution containing about 2% to about 10% by volume alcohol. The concentration of the peracetic acid may range, for example, from about 0.05% by volume to about 1.0% by volume. Most preferably the concentration of the peracetic acid is from about 0.1% to about 0.3% by volume. When the peracetic acid content is about 0.2%, the renal capsular film can be exposed for about two hours. The exposure time can of course be longer or shorter, depending upon the particular agent used, its concentration, and other factors within the purview of those skilled in the art.

Another preferred purification procedure of the invention involves exposing the isolated renal capsule to diluted perpropionic acid. Perpropionic acid is diluted in water or in an aqueous solution of about 2% to about 30% by volume alcohol. Most preferably the alcohol is ethanol. The concentration of perpropionic acid may range from about 0.1% to 10% by volume. More preferably, the perpropionic acid concentration is from about 0.1% to 1% by volume and most preferably from about 0.2% to 0.5% by volume. The exposure time is typically in the range of 0.5 hours to 8 hours. Within the prescribed concentration of perpropionic acid, pH adjustment is not necessary.

Yet another preferred procedure of the invention is exposing the renal capsule to dilute hydrogen peroxide. The hydrogen peroxide can be diluted in water or in an aqueous alcohol solution of about 2% to about 30% by volume alcohol. Most preferably, the alcohol is ethanol. The concentration of hydrogen peroxide can range from about 0.05% to 30% by volume. More preferably, the hydrogen peroxide concentration is from about 1% to 10% by volume and most preferably from about 2% to 5% by volume. The solution may or may not be buffered to a pH from about 5 to 9; more preferably, the solution is buffered to a pH of about 6 to 7.5. The solution temperature can range from about 15 to 50° C. More preferably, the solution temperature is from about 20 to 40° C. Most preferably, the solution temperature is from about 32 to 37° C. The exposure time can range from about 10 to 400 minutes. Preferably, the exposure time is from about 120 to 240 minutes. More preferably, the exposure time is from 180 to 210 minutes. When hydrogen peroxide is employed, the matrix as a whole has greater porosity as well as a higher oxygen content.

Still another purification procedure is exposing the renal capsule to chlorhexidine (1,6-di-(4-chlorophenyldiguanido) hexane) in its digluconate form. The concentration of chlorhexidine digluconate may range from about 0.1% to 15% by weight. More preferably, the chlorhexidine digluconate concentration is from about 0.1% to 2% by weight and most preferably from about 0.2% to 5% by weight. The solvent may be water or an aqueous alcohol solution containing about 2% to about 20% by volume alcohol. Most preferably the alcohol is ethanol and is at a concentration of about 5% to 10%. The solution may or may not be buffered to a pH from about 5 to 8. More preferably the pH is from about 5.5 to 7. The solution temperature may range from about 15 to 30° C. The exposure time may range from about 10 to 400 minutes. More preferably the exposure time is from about 30 to 60 minutes.

Still another method to purify the capsular tissue involves contacting the tissue with a hypertonic decellularization solution, for example, either approximately 1.0 N saline or ethylenediaminetetraacetic acid (EDTA), for periods of time ranging from approximately 10 minutes to 4 hours. The solution may or may not be buffered to a pH from about 5 to 8. More preferably the pH is from about 5.5 to 7. The solution temperature may be any temperature suitable for the tissue processing, and illustratively may range from about 4 to 30° C.

Variations on the purification process can also include one or a combination of the following:

1. Submerging the renal capsule in a solution containing 0.2% peracetic acid and 5% alcohol (e.g. ethanol or denatured alcohol) for two hours under vigorous agitation. The solution to renal capsule ratio is 10:1 by weight. The solution has a pH of 2.6.
2. Submerging the renal capsule in a solution containing 1% peracetic acid and 25% ethanol or denatured alcohol for one hour under vigorous agitation. The solution to renal capsule ratio is 5:1 by weight. The solution has a pH of 2.
3. Submerging the renal capsule in a solution containing 1% peracetic acid, 15% ethanol or denatured alcohol, and 10% hydrogen peroxide for one hour under vigorous agitation. The solution to renal capsule ratio is 5:1 by weight.
4. Submerging the renal capsule in four changes of high purity water for 15 minutes each change. Then subjecting the renal capsule to 1.5 MRAD Electron Beam radiation.
5. Submerging the renal capsule in four exchanges of high purity water for 15 minutes each change. Then subjecting the renal capsule to high-intensity pulsed light.
6. Submerging the renal capsule material in a solution containing 1.0 N saline for two hours under vigorous agitation. Then subjecting the renal capsule to a solution containing 2% hydrogen peroxide and 5% alcohol for three hours under vigorous agitation. The solution to renal capsule ratio is 10:1 by weight.

Further, preferred tissue processing techniques will be used to not only remove cell and cell debris, but also possible endogenous viruses, prion agents, and any contaminants introduced during harvesting of the renal capsule tissue. Illustratively, prion inactivation can be undertaken using sodium hydroxide treatment. Suitably, the tissue can be contacted with a solution of sodium hydroxide for a period of time sufficient to inactivate any prions present. The duration of contact will of course vary with the concentration of the sodium hydroxide solution, and potentially other factors known to those practiced in the relevant art. Illustratively, the tissue may be contacted with a 0.1 N sodium hydroxide solution for 5 minutes to 5 hours, more preferably for 10 minutes to 2 hours, and most preferably for 15 to 60 minutes. Alternatively, more concentrated solutions of sodium hydroxide may be used, e.g. by contacting the tissue with 1.0 N sodium hydroxide for about 15–60 minutes. Still other prion inactivation treatments are known and can be used, including for example the use of steam sterilization under pressure, contact with a sodium hypochlorite solution (e.g. 2.5%), and the like.

Capsular tissue from normal mammalian tissue can further be processed to remove the Galactosyl-alpha(1,3)galactose (Gal epitope) epitope, a glycosyl modification of cell surface components and some serum proteins in all mammals, except humans and Old World primates. General methodologies for preparation of Gal epitope modified tissue have been described in U.S. Pat. No. 6,331,319, the disclosure of which is expressly incorporated herein by reference.

The decellularizing agent and any other processing agents are desirably removed from the renal capsule ECM. For example, it is preferred for some applications, including medical applications, that the purified renal capsule extracellular matrices exhibit a concentration of decellularizing agent and other processing chemical of less than 100 ppm of dried weight. In one embodiment, the decellularizing agent and/or other processing chemicals are extracted by submersion of the disinfected renal capsular tissue in several exchanges of an extracting solvent. The preferred extracting solvent will have an affinity for the processing agents, and have no substantial degrading effect on the ECM. Examples of such solvents include, but are not limited to, aqueous alcohol, saline, sterile water; and among these, sterile water is most preferred. If aqueous alcohol is used, preferably it is the same aqueous alcohol solvent used in the disinfecting solution. Typically, the total immersion period is at least about 60 minutes, more typically it is in the range of about 60 minutes to about 5 hours. The necessary number of solvent exchanges depends on the concentration of the disinfecting and processing agents, and generally ranges from about three (3) to ten (10). In one embodiment of the process of the present invention, five exchanges of the extracting solvent are used. In addition, the suspension is preferably agitated constantly during the immersion period.

The purified renal capsule ECMs resulting from the above described purification process are ready for immediate use or may be stored for future use. The purified ECMs may be stored refrigerated or frozen in a hydrated state, or they may be stored dried. Freeze/thaw cycles are not expected to elicit any substantial detrimental effect to the ECM tissue. Similarly, beneficial properties of the renal capsule ECMs are retained upon drying, for example by lyophilization, and subsequent rehydration. As an example, a dried sheet of renal capsule ECM can be obtained by spreading the purified ECM film on a planar surface and lyophilizing the sheet overnight. While drying by lyophilization is preferred, other methods which are able to preserve the three-dimensional structure of the renal capsule ECMs may also be used. The dried structure can thereafter be reconstituted with aqueous media prior to use, or alternatively it can be implanted or otherwise used in the dried state.

In one specific embodiment where the renal capsule is harvested from an adult pig and treated with peracetic acid, the purified ECM, in its hydrated state, measures approximately 80 μm in thickness. This purified renal capsular film is slightly thinner than the corresponding native, untreated capsular film. Additionally, the purified ECM film exhibits two distinctive sides, a denser side which corresponds to the outer side and a more areolar side which corresponds to the inner side of the native capsule. Furthermore, the preferred treated ECM sheet exhibits a tensile strength of at least about 2 MPa, more preferably of at least about 4 MPa, and typically about 4 to 20 MPa, as measured by a tensile pull test.

The preferred purified renal capsule derived ECM is a substantially acellular material composed almost entirely of collagen. Elastic fibers have also been observed in assays to date utilizing Verhoff's stain. Additionally, the preferred, purified renal capsule tissue has a nucleic acid content of less than about 2 micrograms per milligram, more preferably less than 1 microgram per milligram; a bioburden level less than 2 colony forming units per gram wet weight, more preferably less than 1 colony forming unit per gram; an endotoxin level of less than about 20 EU/g wet weight, more preferably less than about 12 EU/g, and even more preferably less than about 5 EU/g; and a virus level of less than 1 PFU/g wet weight, more preferably less than $1 \times 10^{-3}$ PFU/g. Purified renal capsule tissue having an endotoxin level of less than about 1 EU/g and a virus level of less than about $1 \times 10^{-6}$ PFU/g will be most preferred, particularly for medical applications.

The preferred preparative processes of the present invention thus yield a sheet of renal capsule ECM which possesses excellent mechanical strength and which is medically acceptable, for example, for use in tissue graft prosthesis devices. Illustrative such devices are discussed below; however, it will be understood that the described devices are exemplary, and that those practiced in the area will be able to adapt renal capsule ECMs of the invention to a wide variety of configurations and forms for medical use.

Figure 2:
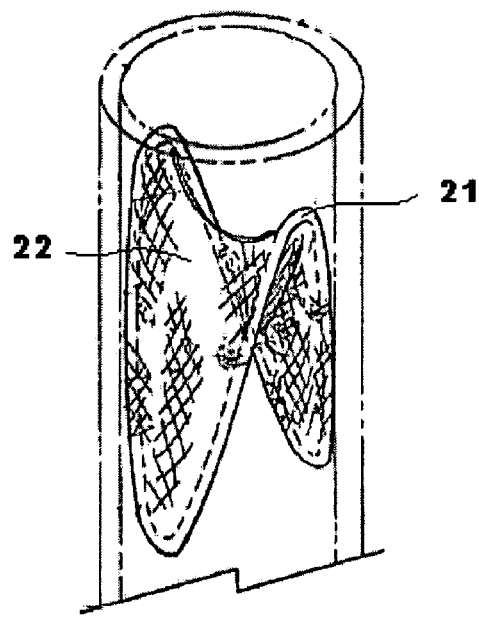
FIG. 2 shows a stent valve device of the invention.

In certain embodiments of the invention, it is contemplated that the purified renal capsule ECMs of the present invention can be formed into tissue grafts taking the forms of powders, fluidized compositions, sheets, tubes, pouches, multi-ply constructs, single-ply constructs, and constructs in combination with other medical devices or implements such as stents, valves, catheters, sutures, staples, balloons, metal coils, synthetic meshes, biodegradable polymers, inert polymers, non-biodegradable polymers, other collagenous matrices, cells such as stem cells, progenitor cells, established cell lines, primary cells (including autogenic, allogenic and xenogenic cells relative to an intended graft recipient), vectors for gene delivery, other naturally-occurring, synthetic, or recombinant bioactive molecules, or in combination with other combinations of these medical devices or implements. For example, renal capsule membrane tissue may be used in inner and/or outer coverings for stents for use in the vasculature or other body passageways. Renal capsule membrane tissue may also be used in the manufacture of stent valve devices. Illustratively, shown in FIG. 2 is a stent valve device including a multiple sided stent 21 having renal capsule membrane tissue 22 attached thereto to form a bi-leaflet stent valve analagous to those described in WO0156500. These and other renal capsule membrane stent cover and stent valve device configurations analogous to those described in _WO156500, WO154625, and WO985545 are contemplated as a part of the present invention.

The purified renal capsule ECMs of the present invention can be formed into a powder tissue graft composition. The renal capsule ECMs can be desirably comminuted by tearing, cutting, grinding, shearing or the like, frozen or not, in a manner similar to that described for other collagen-based ECMs in U.S. Pat. No. 5,275,826, International Publications Nos. WO 96/32146, WO 98/22158 and WO 98/25636; the disclosures of which are expressly incorporated herein by reference. Grinding the renal capsule ECMs in a frozen or freeze-dried state is advantageous, although good results can be obtained as well by subjecting a suspension of pieces of the renal capsule ECMs to treatment in a high speed blender and dewatering, if necessary, by centrifuging and decanting excess waste. The comminuted renal capsule ECMs can then be dried, for example freeze dried, to form a powder.

In one illustrative preparation, the renal capsule ECMs prepared as described herein are reduced to small pieces (e.g. by cutting) and then quickly frozen with liquid nitrogen and then comminuted under liquid nitrogen to form a coarse powder. Such processing can be carried out, for example, with a manual arbor press with a cylindrical brass ingot placed on top of the frozen renal capsule tissues. The ingot serves as an interface between the tissues and the arbor of the press. Liquid nitrogen can be added periodically to the renal capsule tissue to ensure the tissues remain in frozen state. The coarse powder is further ground using a pre-chilled mortar and pestle to produce a consistent, more finely divided product. Again, liquid nitrogen is used as needed to maintain solid frozen particles during final grinding.

Thereafter, if desired, the powder can be suspended in water or buffered saline and optionally other pharmaceutically acceptable excipients, to form a fluid tissue graft composition, e.g. having a viscosity of about 2 to about 300,000 cps at 25° C. The higher viscosity graft compositions can have a gel or paste consistency. Alternatively, the particulate composition can be lyophilized overnight and sterilized to form a solid substantially anhydrous particulate composite.

In orthopedic applications, renal capsule ECM powders of the invention can be used to repair bone tissue, for instance using the general techniques described in U.S. Pat. No. 5,641,518. Thus, a powder form of the renal capsule ECMs can be implanted into a damaged or diseased bone region for repair. The renal capsule ECMs powder can be used alone, or in combination with one or more additional bioactive agents such as physiologically compatible minerals, growth factors, antibiotics, chemotherapeutic agents, antigen, antibodies, enzymes, vectors for gene delivery and hormones. Preferably, the powder-form implant will be compressed into a predetermined, three-dimensional shape, which will be implanted into the bone region and will substantially retain its shape during replacement of the graft with endogenous tissues.

The purified renal capsule ECMs of the invention may be fluidized following techniques as described in U.S. Pat. No. 5,275,826, the disclosure of which is incorporated herein by reference. Fluidized form of the renal capsule ECMs are generally prepared by solubilization by enzymatic digestion, including the use of protease, such as trysin or pepsin, or other appropriate enzymes such as a collagenase, glycosaminoglycanase, or hyaluronidase, or the use of a mixture of enzymes, for a period of time sufficient to solubilize the tissue and form a substantially homogeneous solution. While a fluidized composition may be formed from enzyme digestion of comminuted tissues, a procedure involving only enzyme digestion with no mechanical commination can also be used.

In one illustrated embodiment of preparing fluidized composition of renal capsule ECMs, renal capsule ECM powder prepared as described above is sifted through a wire mesh, collected, and subjected to proteolytic digestion with 1 mg/ml of pepsin (Sigma Chemical Co., St. Louis, Mo.) and 0.1 M acetic acid, adjusted to pH 2.5 with HCl, over a 48 hour period at room temperature forming a substantially homogeneous solution. After this treatment, the reaction medium is neutralized with sodium hydroxide to terminate the peptic activity. The solubilized renal capsule ECMs are then concentrated by salt precipitation. The precipitate may be freeze-dried to form a fluidized powder.

The renal capsule ECMs can be formed into sheet constructs. For example, the purified renal capsule ECMs can be spread out into their native sheet form, trimmed to size if desired, and lyophilized. Multi-layer sheet constructs can be made including two or more such sheets stacked directly atop one another. In this regard, these constructs can be stabilized by bonding the collagen sheets together, for example by compressing the sheets under dehydrating conditions, use of crosslinkers such as 1-ethyl-3-(3-dimethylaminopropyl) carboduimide (EDC), or other suitable means. In these and other multi-layer constructs described herein, the renal capsule ECM sheets or strips may be stacked or arranged such that their inner surfaces contact one another, or such that their outer surfaces contact one another, and/or such that an inner surface of one ECM sheet contacts an outer surface of another ECM sheet. Thus, overall multi-layer constructs can be fabricated which present outer faces each formed from an inner (more areolar) surface of a renal capsule ECM, outer faces each formed from an outer (more dense) surface of a renal capsule ECM, or one outer face formed from an inner surface of a renal capsule ECM and outer one face formed from an outer surface of a renal capsule ECM. Still further, where the overlapped ECM sections are not exactly contiguous with one another, one or both outer faces of the overall multi-ply construct may present both inner and outer surfaces of renal capsule ECM.

Larger area sheet constructs can be prepared by overlapping and fusing together of several smaller area sheets. The construction of a large area sheet from smaller area sheets has been described in U.S. Pat. No. 5,127,903, International Publication No. WO 96/32146, *ASAIO Journal,* 2000, 46:268–272, and the disclosures of these are expressly incorporated herein by reference. In one embodiment, the small area sheets are fused together by compressing the overlapped edges of these sheets under dehydrating conditions. In another embodiment, the sheets are joined by photocrosslinking in the presence of a photo-catalytic dye. Other standard tissue bonding techniques known to those skilled in the art, including the use of sutures, crosslinking agents, adhesives and pastes can also be used.

The renal capsule derived matrices can be configured into tubes of various dimension and thickness to provide tubular tissue grafts useful in, for example, vascular and urinary tract replacements. Techniques for making tubular grafts from collagenous sheets have been generally described in U.S. Pat. Nos. 2,127,903 and 4,902,508 and International Publication No. WO 98/22158, the disclosures of which are expressly incorporated herein by reference. Illustratively, a tubular graft may be constructed by manipulating sheets of the renal capsule ECMs to define a tube and suturing, bonding or otherwise securing the longitudinal seam to form an appropriately-dimensioned tubular graft having a lumen. In addition, the tube may be formed so as to present a luminal or outermost surface composed of the outer (more dense) side of the renal capsule ECM, and/or the inner (more areolar) side of the renal capsule ECM. In one embodiment, the tubular construct is formed over a sterile rod or mandrel having an outer diameter approximating that of the recipient vessel to be grafted. Preferably, at least one sheet layer of the inventive renal capsule ECM is wrapped about the rod to form an overlapping seam. The overlapped seam may be joined together by any of the conventional methods such as suturing, photocrosslinking, chemical crosslinking, crosslinking by enzymatic means, radiation crosslinking, fusion under compression and dehydration, or by adhesives and the like. It is further understood that the tubular grafts may be constructed from multiple layers of purified renal capsule ECMs, with the number of layers used generally depending on the strength requirement of the particular application. Alternatively, multiple layered grafts may consist of layers of purified renal capsule ECMs laminated in combination with other collagen-based materials from other sources, such as submucosal tissues obtained from intestine, uterus, urinary bladder, or stomach, pericardial tissue, and the like. For example, vascular grafts are typically constructed with multiple layers of ECM sheets to ensure that they can withstanding the constant pulsating pressure of their implanting environment. For vascular, urinary tract, or other body lumen applications, renal capsule ECMs of the invention can be used as exterior, interior or other coverings for supporting structures such as stents. These applications include, for example, use with self-expanding or otherwise expandable stents, both to form biocompatible coverings generally and to form valve structures (see, e.g. WO9962431 published Dec. 9, 1999 and WO119285 published Mar. 22, 2001, both hereby incorporated herein by reference). In one mode of forming a valve structure, the renal capsule ECM can be attached to a stent in a fashion whereby it forms one, two, or more leaflets, cusps, pockets or similar structures that resist flow in one direction relative to another. In a specific application of such devices, such devices constructed as vascular valves are implanted to treat venous insufficiencies in humans, for example occurring in the legs. In an alternate approach, valves for treating these or other valve deficiencies may be surgically created without the use of a stent or other supporting structure.

The renal capsule extracellular derived matrices can optionally be preconditioned for orthopedic applications.

Preparation of orthopedic grafts have been generally described in U.S. Pat. Nos. 2,127,903; 5,281,422; 5,275,826; and 5,352,463, the disclosures of which are expressly incorporated herein by reference. Conditioning alters the viscoelastic property and reduces the strain inherent in the native ECMs sheets. The renal capsule ECMs may be conditioned by stretching, chemical treatment, enzymatic treatment or exposing the tissue to other environmental factors, or any other art known methods. Preferably, the ECMs are conditioned by stretching under a load to a predetermined percentage of the pre-stretched length. For example, the renal capsule ECMs may be conditioned by suspending a weight from a segment of an ECM sheet for a period of time sufficient to allow about 10% to about 20% elongation of the segment. The renal capsule ECM segment can then be configured, alone or in combination with other segments, to a variety of shapes to serve as orthopedic grafts.

In one area of orthopedic use, renal capsule ECMs of the invention can be used for the repair and/or replacement of connective tissues. Connective tissues for the purposes of the present invention includes bone, cartilage, muscle, tendons, ligaments, and fibrous tissue including the dermal layer of skin. For example, the renal capsular derived ECMs may serve as ligament or tendon replacement or a patch for a broken or severed tendon or ligament. Connective tissue repair techniques, which have been applied to other naturally-derived or synthetic graft materials and generally described in U.S. Pat. Nos. 2,127,903; 5,281,422; 5,275,826; and 5,352,463, can be undertaken using the renal capsule ECM segments.

The renal capsular ECM segments can be formed for surgical attachment to existing physiological structures, including bone, tendon, ligament, cartilage and muscle, using surgically acceptable techniques. For such connective tissue grafting application, the segment is desirably configured to have a layered or multilayered configuration, with at least the opposite end portions and/or opposite lateral portions being formed to have multiple layers of the graft material to provide reinforcement for attachment to the physiological structure. In a ligament replacement application, opposite ends will be attached to first and second bones, respectively, the bones typically being articulated as in the case of a knee joint. In a tendon replacement application, a first end of the graft construct will be attached to a bone, and a second end will be attached to a muscle.

As indicated above, in connective tissue applications, it will be advantageous to form, manipulate or shape the end portions of the graft construct to be attached, for example, to a bone structure, in a manner that will reduce the possibility of graft tearing at the point of attachment. For these purposes, the conditioned renal capsule ECM graft material can be folded or partially everted to provide multiple layers for gripping, for example, with spiked washers or staples. Alternatively, a renal capsule ECM segment can be folded back on itself to join the end portions to provide a first connective portion to be attached, for example, to a first bone and a bend in the intermediate portion to provide a second connective portion to be attached to a second bone articulated with respect to the first bone. For example, one of the end portions of the renal capsule ECM graft can be adapted to be pulled through a tunnel in, for example, the femur and attached thereto, while the other of the end portions may be adapted to be pulled through a tunnel in the tibia and attached thereto to provide a substitute for the natural cruciate ligament, the segment being adapted to be placed under tension between the tunnels to provide a ligament function, i.e., a tensioning and position function provided by a normal ligament.

Furthermore, renal capsule ECM sheets of the present invention can also be used to provide an orthopedic graft for use as connective tissue to hold fractured bone pieces together and in proper orientation in the body, the tissue segment being formed to serve as a fracture wrap about segments of fractured bone and to be attached to the bone.

As noted above, tissue grafts designated for orthopedic applications are typically multi-layer constructs. Methods of forming multi-ply constructs are generally known to the art. For example, a simple multi-layer construct may be form by stacking two or more renal capsule ECM sheets and having their end portions joined together. A double walled tube can be formed by pulling one tubular segment internally within another tubular segment and joining the ends. A multi-layer construct can also be form by braiding one segment or strip of renal capsule ECMs in a braided configuration, for example a diamond or sashcord braided configuration, or in a mesh configuration including multiple loops inter-coupled to neighboring loops.

Tissue graft compositions of the invention may be used to treat or repair cardiovascular tissues. For example, tissue graft compositions of the invention may be used to treat cardiac defects, including septal defects.

The graft constructs and compositions prepared can be packaged to protect the purity of the constructs for storage and shipment to the consumers. In one embodiment, dried graft constructs are packaged in pre-sterilized bags and then vacuum sealed and/or heat sealed. These packages may be stored and shipped at room temperature. In another embodiment, graft constructs that are in a hydrated state are packaged in pre-sterilized bags and then vacuum sealed and/or heat sealed. The hydrated samples may be stored and shipped frozen. Preferably, the pre-sterilized bags are formed of materials which are impervious to moisture and oxygen, e.g., PETE. For added assurance that the purity of the construct are maintained, before storage, the sealed packages may be irradiated to decimate pathogens that were inadvertently collected on the surface of the constructs during manufacturing. In yet another embodiment, dried graft constructs can be packaged in non-sterile gas permeable bags and then vacuum sealed and/or heat sealed. The packaged constructs are then sterilized along with the gas permeable packaging using ethylene oxide gas. It is contemplated that still other conventional techniques for sterilization which are within the knowledge of those of ordinary skill in the art may also be used.

The preferred purified renal capsule derived ECM material contains residual compositionally bioactive proteins. For example, analysis of such ECM materials to date has shown that they contain Fibroblast Growth Factor 2 (basic FGF), and vascular endothelial growth factor (VEGF). It is also expected that preferred purified ECM materials of the invention may contain additional bioactive proteins including, for example, one or more of glycosaminoglycans, glycoproteins, proteoglycans, cytokines and/or growth factors.

Tissue graft compositions including renal capsule ECMs can be administered to a vertebrate host in an amount effective to induce endogenous tissue growth at a site in the host in need of same due to the presence of damaged or diseased tissue. It is contemplated that the vertebrate host may be xenogenic to the animals from which the renal capsule ECMs were harvested. The renal capsule ECM compositions can be administered to the host in either solid or sheet form, by surgical implantation alone or in combination with other art-recognized implant compositions, or in fluidized form, by injection.

The potential applications include, but are not limited to, vascular grafts, orthopedic soft tissue implants, wound dressings, urogenital and other body wall repairs. It is further anticipated that the renal derived ECM can be utilized as a cell growth substrate for in vitro cultivation of eukaryotic cells, for research or to generate cell-seeded graft devices for implantation. These applications employ techniques in the art which have been applied to other naturally-derived ECMs or synthetic graft materials and can be undertaken using the purified renal capsule derived ECMs of the present invention.

Fluidized renal capsule ECMs of this invention would find many orthopedic applications, e.g. tissue replacement, augmentation, and/or repair. It is contemplated that fluidized renal capsule ECMs of the present invention may be used as an injectable heterograft. By injecting an effective amount of a fluidized renal capsule ECMs composition into the location of a tissue defect, for example, in bone or soft tissues in need of repair or augmentation, one can readily take advantage of the biotropic properties of the renal capsule ECMs. It is further contemplated that the fluidized composition can be used advantageously as a filler for implant constructs, e.g., in cosmetic or trauma-treating surgical procedures.

Renal capsule ECMs of the invention can also be used in body wall repair, including for example in the repair of abdominal wall defects such as hernias, using techniques analogous to those described in *Ann. Plast. Surg.,* 1995, 35:374–380; and *J. Surg. Res.,* 1996, 60:107–114. In such applications, preferred renal capsule ECM tissue grafts of the invention promote favorable organization, vascularity and consistency in the remodeled tissue.

In dermatological applications, renal capsule ECMs of the invention can be used in the repair of partial or full thickness wounds and in dermal augmentation using general grafting techniques which are known to the art and literature (see, e.g. Annals of Plastic Surgery 1995, 35:381–388). In addition, in the area of burn treatment, it is generally known to provide a dermal substitute onto which cultured epidermal grafts (preferably cultured epidermal autografts, or CEA's) are transplanted. Such cultured grafts have typically involved transplanting keratinocytes and/or fibroblasts onto the dermal substitute. In accordance with the present invention, the purified renal capsule ECMs can be used as the dermal substitute, for example in sheet form, and the CEA accordingly transplanted onto the renal capsule ECMs. In one embodiment of practicing this aspect of the invention, keratinocytes can be transplanted, for example by seeding or transferring a keratinocyte sheet, onto the denser side of the renal capsule ECM sheet and fibroblasts can be transplanted also on the more areolar side of the renal capsule ECM sheet.

Renal capsule ECMs of the invention can also be used in tissue grafts for urogenital applications For instance, a large area renal capsule ECM sheet can be used for the repair of urinary bladder, in which the renal capsule ECM sheet provides a scaffold for bladder tissue regeneration. The techniques for urinary bladder repair have been generally described in U.S. Pat. No. 5,645,860; Urology, 1995, 46:396–400; and J. Urology, 1996, 155:2098; the disclosures of which are expressly incorporated herein by reference.

The inventors further contemplate that tubular grafts including renal capsule ECMs may be used for the repair and replacement of the urinary tract. A tubular graft of a specific diameter and strength, the making of which has been previously described, can be surgically substituted for a damaged or diseased urinary tract by standard surgical techniques. Technique for urinary tract replacement has been described generally in "Use of Reconstructed Small Intestine Submucosa for Urinary Tract Replacement", by Xie et. al, in *ASAIO Journal* 2000, p. 268, and the disclosure of which is expressively incorporated herein by reference. It has been shown that tubular grafts, constructed from extracellular matrices derived from the small intestinal submucosa, implanted into swine to replace segments of excised ureter induce bio-remodeling. Two weeks after implantation, fibroblasts and mononuclear cells had infiltrated the grafts, neovascularization had occurred. The inventors contemplate the tissue grafts prepared from renal capsule extracellular matrices will induce similar bioremodeling.

In fluidized form, the inventive renal capsule ECMs can also find use in an endoscopic injection procedure to correct vesicureteral reflux. In such applications, a submucosal injection can be made, for instance in the area under the ureteral orifice of a patient, to induce smooth muscle growth and collagen formation at the injection site.

It is contemplated that tissue graft constructs formed with renal capsule ECMs of the present invention can be used in neurological applications. For example, in techniques requiring a dural substitute to repair defects due to trauma, tumor resection, or decompressive procedures. It is also contemplated that renal capsule ECMs of the invention can be used as adhesion barriers in surgical applications.

The renal capsule ECMs of the invention can be used for supporting proliferation and inducing differentiation of eukaryotic cells cultured in vitro. Procedures for utilizing collagen based ECMs for in vitro culturing of cells have been described in International Publication No. WO 96/24661, the disclosure of which is expressly incorporated herein by reference. Generally, the method includes the step of introducing eukaryotic cells, e.g. endothelial, fibroblastic, fetal skin, osteosarcoma, and adenocarcinorma cells, in vitro, to a composition of renal capsule ECMs under conditions conducive to the growth of the eukaryotic cells. Renal capsule ECMs in sheet, paste or gel form can be used. Typically, the renal capsule ECM composition is combined with various nutrients, growth factors, minerals and salts known in the art to be important for the particular cell types. Furthermore, renal capsule ECMs can be combined with current available cell culture media to enhance the effectiveness of such media to induce growth, proliferation and differentiation of various cell types.

The inventive renal capsule ECMs can also serve as a collagenous matrix in compositions for producing transformed cells. The techniques for cell transformation have been described in International Publication Nos. WO 96/25179 and WO 95/22611; the disclosures of which are expressly incorporated herein by reference. Preferably, purified renal capsule ECMs of the present invention, for example in fluidized or paste form, is included in the cell transformation compositions, in combination with a recombinant vector (e.g. a plasmid) containing a nucleic acid sequence with which in vitro or in vivo target cells are to be genetically transformed. The cells targeted for transformation can include, for example, bone progenitor cells.

In order to promote a further understanding of the present invention and its features and advantages, the following specific examples are provided. It will be understood that these specific examples are illustrative, and not limiting, of the present invention.

EXAMPLE 1

The tissue graft material of this invention is prepared in accordance with the following steps:

Kidneys including the renal capsule of freshly slaughtered adult pigs are obtained and stored on ice prior to treatment at the laboratory. The capsule is fairly loose, but is attached to the kidney at discrete locations. The fatty tissue that is attached to the capsular tissue is first removed with a blunt dissecting instrument. A single slit is made in the capsule along the long axis of the kidney through the renal pelvis and the attachments between the kidney and the capsule are clipped and the capsule is peeled away from the kidney. Any remaining fatty tissues which are still attached to the capsules are carefully removed. The isolated capsule is semi-translucent.

The isolated capsule is rinsed several times with sterile water and then disinfected by submerging it in an aqueous ethanol peracetic acid solution for two hours and under vigorous agitation. The peracetic acid solution contains 0.2% by volume of peracetic acid, 5% by volume of ethanol and has a pH of 2.6. The weight ratio of disinfecting solution to renal capsule placed therein is approximately 10:1.

Subsequent to the disinfecting treatment, peractic acid and other processing chemicals are extracted from the renal capsule tissue with sterile water. The renal capsules are submerged in five exchanges of sterile water, for a period of 15 minutes each and under vigorous agitation. The hydrated capsular tissue material is stored refrigerated.

It is found that the peracetic acid treated (purified) renal capsule material is thinner and less cellular than the native material. In its hydrated state, the tissue measures about 80 μm. Additionally, the material has a dense side and a more areolar side, and has cellular debris and nuclei substantially depleted as compared to non-purified renal capsule.

EXAMPLE 2

Samples of the purified tissue as prepared in Example 1 are stained using Gomori's Trichome stain. It is found that the material is primarily collagenous.

EXAMPLE 3

Samples of the purified tissue as prepared in Example 1 are stained using Verhoff's stain. Histological study reveals a presence of elastic fibers in the purified renal capsule tissue which is indicative of isolated renal capsule and separation from the surrounding mesenteric tissues.

EXAMPLE 4

The mechanical property of renal capsule derived ECMs has been evaluated using a standard bench top tensile tester. The test involves the placement of two ends of a dried ECM strip between opposing clamps of the instrument. The clamps are mechanically driven apart in opposing directions at a steady speed, thereby pulling the specimen apart until the point of failure. The load necessary to maintain the pulling rate corrected for elongation is indicative of the tensile strength of a material.

Specimens of the purified tissue as prepared in Example 1 are removed from refrigerated storage and spread into sheet form and freeze-dried. Testing strips, each about 1 cm wide and about 4 to 4.5 cm long, are cut from the dried ECMs specimen. The ends of the test strip are placed between folded file folder pieces and the sandwiched strip is clamped between the jaws of the instrument and secured. The clamps are set to move apart in opposing directions at a rate of approximately 10.00 mm/minute. The accumulated data from 3 separate test strips of a single specimen of renal capsule derived ECM are presented in Table 1. The load required to maintain the pulling speed vs. the elongation of the test strip is plotted in FIG. 1.

|         | Max Load (N) | Ext at Break (mm) |
|---------|--------------|-------------------|
| 1       | 7.55         | 20.33             |
| 2       | 10.60        | 11.82             |
| 3       | 6.59         | 20.00             |
| Mean    | 8.25         | 17.38             |
| S.D.    | 2.09         | 4.82              |
| minimum | 6.59         | 11.82             |
| maximum | 10.60        | 20.33             |

EXAMPLE 5

In this Example, porcine renal capsule (RCM) was analyzed by a standard ELISA/absorbance assay for Fibroblast Growth Factor 2 and Vascular Endothelial Growth Factor (VEGF). Samples of raw renal capsule membrane, and disinfected renal capsule membrane processed as in Example 1, were extracted in 2M urea containing 2.5 mg/ml heparin. The extracted lyophilisate was resuspended in sterile water at a concentration of 10 mg/ml. ELISA/absorbance analysis of standards and samples of the extracts revealed the presence of FGF-2 and VEGF as follows:

| Sample          | FGF-2              | VEGF                  |
|-----------------|--------------------|-----------------------|
| Disinfected RCM | 56.68 ± 4.48 ng/g  | 334.06 ± 168.8 pg/g   |
| Raw RCM         | 179.0 ± 3.44 ng/g  | 1947.88 ± 217.2 pg/g  |

EXAMPLE 6

Samples of porcine renal capsule, disinfected as described in Example 1, were assessed for acute systemic toxicity in the mouse. In particular, the samples were extracted in 0.9% sodium chloride USP solution and cottonseed oil, NF. These extracts were evaluated for systemic toxicity in accordance with requirements of the International Organization for Standardization 10993: Biological Evaluation of Medical Devices, Part 11: Tests for Acute Systemic Toxicity. A single dose of the appropriate test article extract was injected into each of five mice per extract by either the intravenous or intraperitoneal route. Similarly, five mice were dosed with each corresponding reagent control. The animals were observed immediately and at 4, 24, 48 and 72 hours. No mortality or evidence of systemic toxicity was observed for the extracts, which met the requirements of the test.

EXAMPLE 7

A sample of porcine renal capsule disinfected as in Example 1 was subjected to an in vitro biocompatibility study, based on the International Organization for Standardization 10993: Biological Evaluation of Medical Devices, Part 5: Tests for Cytotoxicity: in vitro Methods guidelines, to determine the potential for cytotoxicity. A single extract of the test sample was prepared using single strength Minimum Essential Medium supplemented with 5% serum and 2% antibiotics (IX MEM). This test extract was placed onto three separate confluent monolayers of L-929 mouse fibroblast cells propagated in 5% $CO_2$. Three separate monolayers were prepared for the reagent control, negative control and for the positive control. All monolayers were incubated at 37° C. in the presence of 5% $CO_2$ for 48 hours. The monolayer in the test, reagent control, negative control and positive control wells were examined microscopically at 48 hours to determine any change in cell morphology.

Under the cell conditions of this study, the 1×MEM test extract showed no evidence of causing cell lysis or toxicity. The 1×MEM test extract met the requirements of the test since the grade was less than a grade 2 (mild reactivity). The reagent control, negative control and the positive control performed as anticipated.

EXAMPLE 8

A sample of disinfected porcine renal capsule was subjected to a hemolysis assay as follows. The sample was added to saline. Diluted rabbit blood was added to the sample in saline. This combination was evaluated to determine whether direct contact with the test article would cause in vitro red blood cell hemolysis.

Blood was obtained from three rabbits, pooled, diluted and added to duplicate tubes of the test article in saline. A negative control and positive control were similarly prepared. Each tube was inverted gently to uniformly mix the contents with the blood. The tubes were then maintained in a stationary position for 4 hours and 37° C. Following incubation, the suspensions were mixed gently, transferred to conical tubes, and centrifuged. The resulting supernatant was added to Drabkin's reagent. The percent transmission of the extract was spectrophotometrically measured at a wavelength of 540 nm.

Under the conditions of this study, the mean hemolytic index for the sample in saline was 0%. The sample was nonhemolytic. The negative and positive controls performed as anticipated.

EXAMPLE 9

Renal capsule membrane (RCM) and polypropylene mesh (PPM) were compared in a model of rat full-thickness muscle/fascia ventral abdominal body wall repair. During surgery, the complete thickness of the rat abdominal wall was removed and the defect was repaired with either RCM or PPM. The omentum was either left intact or completely removed during the surgery and the four groups compared histologically after 4 weeks.

After 4 weeks the RCM grafts were highly vascularized with extensive infiltration of fibrovascular tissue. The general response to this biomaterial was the development of a thick, moderately cellular, fibrovascular layer on both the subcutaneous and mesothelial surfaces of the biomaterial; this fibrous connective tissue infiltrated and replaced the biomaterial. An influx of lymphocytes and plasma cells was evident, with occasional aggregates of hemosiderin-laden macrophages, principally on the subcutaneous side of the material (a response to hemorrhage at the surgical site).

The host's reaction to the polypropylene mesh was very different from the reaction to the RCM biomaterial. The reaction in the presence of PPM was characterized by a foreign body, granulomatous inflammatory response surrounding the meshwork with early fibrosis developing in the loose adipose tissue that filled the spaces of the mesh. Fibrous connective tissue appeared to develop from the subcutaneous tissue and span the defect; it rarely infiltrated the implant. This was in marked contrast to the reactions seen in the RCM groups, where the biomaterial was infiltrated and replaced with fibrous connective tissue in a manner more consistent with the natural wound healing process.

EXAMPLE 10

Renal capsule matrix was evaluated in a model of subcutaneous implantation. A sheet of RCM was implanted into a pouch created in the dorsum of a rat and was allowed to remodel for 14 days. No rats exhibited signs of complications. After 14 days the tissues were explanted and evaluated histologically. The RCM was populated with extensive cellular infiltrate and contained evidence of extensive vascularity. The infiltrate was exclusively mononuclear in nature with no evidence of giant cell formation or other signs of immunologic rejection.

EXAMPLE 11

Renal capsule matrix as prepared in Example 1 was evaluated in an orthopedic model of Achilles tendon repair. Twenty rats underwent surgical excision of a 5-mm section of the Achilles tendon In ten of the rats, the tendon stumps were approximated and sutured loosely together, leaving the defect unfilled. In the other ten rats, the tendon ends were joined tightly with a renal capsule matrix graft. In both groups, the rats were allowed to recover and use their limbs following surgery. They were observed clinically for the ability to use the experimentally manipulated limb for four weeks. After four weeks, all animals were euthanized and the tendons collected, fixed, and examined histologically for evidence of repair.

Clinical observation revealed that the rats implanted with the renal capsule matrix graft were able to walk after approximately 10 days without observable deficits in their gait, while the rats that had no graft placed were unable to use their limbs following surgery for the duration of the study. Histological assessment after 28 days revealed that the renal capsule matrix grafts had become populated with host-derived cells that had begun to lay down collagenous repair material along the long axis of the tendon. Rats that had not been grafted with renal capsule matrix failed to show organized deposition of collagen but were repaired with unorganized scar tissue material.

While the invention has been detailed in the foregoing description, the same is to be considered as illustrative and not restrictive in character, it being understood that only the preferred embodiment has been shown and described and that all changes and modifications that come within the spirit of the invention are desired to be protected. Further, all publications cited herein are considered indicative of the skills possessed by those in the art, and all such publications are hereby incorporated herein by reference in their entirety.

What is claimed is:

1. A tissue graft prosthesis comprising isolated, decellularized renal capsule tissue.

2. The tissue graft prosthesis of claim 1 wherein said renal capsule tissue is from a warm blooded vertebrate.

3. The tissue graft prosthesis of claim 2 comprising a sheet of renal capsule tissue.

4. The tissue graft prosthesis of claim 3 wherein said sheet of renal capsule tissue exhibits a tensile strength of at least about 2 MPa.

5. The tissue graft prosthesis of claim 3 wherein said sheet of renal capsule tissue has an endotoxin level no greater than 20 endotoxin units per gram.

6. The tissue graft prosthesis of claim 5 wherein said sheet of renal capsule tissue has a bioburden level of less than 2 colony forming units per gram.

7. The tissue graft prosthesis of claim 1 wherein said graft prosthesis is a powder.

8. The tissue graft prosthesis of claim 1 wherein said graft prosthesis is a tube.

9. The tissue graft prosthesis of claim 1 wherein said graft prosthesis is an essentially planar sheet.

10. An article of manufacture comprising isolated, decellularized renal capsule tissue and sterile packaging containing the isolated, decellularized renal capsule tissue.

11. The article of claim 10 wherein said renal capsule tissue is dried.

12. The article of claim 10 wherein said renal capsule tissue is in hydrated form.

13. The article of claim 10 wherein said renal capsule tissue is in sheet form.

14. The article of claim 10 wherein said renal capsule tissue is in powder form.

15. The article of claim 10 wherein said renal capsule tissue is in tubular form.

16. The article of claim 10 wherein said renal capsule tissue is in fluidized form.

17. A method of tissue grafting comprising grafting a mammal with a tissue graft prosthesis including isolated, decellularized renal capsule tissue.

18. The method of tissue grafting of claim 17 wherein said renal capsule tissue is from an animal xenogenic to said mammal.

19. The method of tissue grafting of claim 18 wherein said renal capsule is porcine renal capsule.

20. A tissue graft prosthesis comprising a sheet of renal capsule collagen from a warm-blooded vertebrate, wherein said sheet of renal capsule collagen exhibits a tensile strength of at least about 4 MPa.

21. The tissue graft prosthesis of claim 20, wherein said graft prosthesis is a tube.

22. The tissue graft prosthesis of claim 20, wherein said graft prosthesis is an essentially planar sheet.

23. The tissue graft prosthesis of claim 20 wherein said sheet of renal capsule collagen has endotoxin level no greater than 20 endotoxin units per gram.

24. The tissue graft prosthesis of claim 20, wherein said sheet of renal capsule collagen is dried.

25. The tissue graft prosthesis of claim 20 wherein said warm-blooded vertebrate is selected from the group consisting of porcine, bovine and ovine animals.

26. The tissue graft prosthesis of claim 25, wherein said warm-blooded vertebrate is a pig.

* * * * *